US009023639B2

(12) United States Patent
Kim et al.

(10) Patent No.: US 9,023,639 B2
(45) Date of Patent: May 5, 2015

(54) APPARATUS FOR AMPLIFYING NUCLEIC ACIDS

(75) Inventors: Jae-Young Kim, Seoul (KR); Joong-Hyun Baek, Gyeonggi-do (KR)

(73) Assignee: Samsung Electronics Co., Ltd., Gyeonggi-Do (KR)

(*) Notice: Subject to any disclaimer, the term of this patent is extended or adjusted under 35 U.S.C. 154(b) by 1174 days.

(21) Appl. No.: 12/333,113

(22) Filed: Dec. 11, 2008

(65) Prior Publication Data

US 2009/0186404 A1 Jul. 23, 2009

(30) Foreign Application Priority Data

Jan. 22, 2008 (KR) ........................ 10-2008-0006793

(51) Int. Cl.

*C12M 1/34* (2006.01)
*B01L 7/00* (2006.01)
*B01L 3/00* (2006.01)

(52) U.S. Cl.

CPC ............... *B01L 7/525* (2013.01); *B01L 3/5027* (2013.01); *B01L 3/502707* (2013.01); *B01L 2300/0816* (2013.01); *B01L 2300/087* (2013.01); *B01L 2300/1822* (2013.01); *B01L 2300/1827* (2013.01); *B01L 2400/0487* (2013.01)

(58) Field of Classification Search

CPC ...... C12Q 1/686; C12Q 1/6844; C12Q 1/689; C12Q 1/6853; C12Q 1/6848; C12Q 1/6883; C12Q 1/6827; C12Q 1/6816; C12Q 1/6869; C12Q 2600/156; C12N 15/85; C12N 9/6459; C12N 2830/002; C12N 2830/85; C12N 2840/20; B01L 3/5027; B01L 3/502707; B01L 7/525; B01L 2400/0487; B01L 2300/087; B01L 2300/1822; B01L 2300/1827; B01L 2300/0816

USPC .................. 422/198, 503; 435/6, 91.2, 286.1, 435/286.5, 288.7, 303.1

See application file for complete search history.

(56) References Cited

U.S. PATENT DOCUMENTS 6,679,279 B1 * 1/2004 Liu et al. ......................... 137/13

(Continued)

FOREIGN PATENT DOCUMENTS

| | | |
|---|---|---|
| JP | 2006-061031 | 3/2006 |
| KR | 19990018655 | 6/1999 |
| KR | 10-20030073255 A | 9/2003 |

(Continued)

OTHER PUBLICATIONS

Yarin et al. "Cooling Systems of Electronic Devices" from "Fluid Flow, Heat Transfer and Boiling in Micro-Channels". Springer Berlin Heidelberg. pp. 7-101.*

*Primary Examiner* — Michael Hobbs

(74) *Attorney, Agent, or Firm* — Marger Johnson & McCollom PC

(57) ABSTRACT

Provided is a nucleic acid amplifying apparatus having a uniform distribution of reaction temperature in a reaction space. The nucleic acid amplifying apparatus includes a substrate providing a polymerase chain reaction (PCR) space, and a plurality of heating units disposed above or below the reaction space to transfer heat to the reaction space, wherein the heating unit includes a plurality of heating units arranged substantially in parallel with each other, and among the plurality of heating units, the heating units disposed adjacent outermost portions of the reaction space have the largest heat radiation quantity.

18 Claims, 13 Drawing Sheets

(56) References Cited

U.S. PATENT DOCUMENTS

| | | | | | |
|---|---|---|---|---|---|
| 6,818,185 | B1 * | 11/2004 | Petersen et al. | ............... | 422/547 |
| 2003/0129646 | A1 * | 7/2003 | Briscoe et al. | .................... | 435/6 |
| 2006/0258012 | A1 * | 11/2006 | Yang et al. | ...................... | 436/63 |
| 2009/0061489 | A1 * | 3/2009 | Hanagata et al. | ............ | 435/91.2 |

FOREIGN PATENT DOCUMENTS

| | | | |
|---|---|---|---|
| KR | 10-20060076288 | A | 7/2006 |
| KR | 2006-0092569 | | 8/2006 |
| KR | 2006-0116984 | | 11/2006 |
| KR | 10-20080005224 | A | 1/2008 |

* cited by examiner

APPARATUS FOR AMPLIFYING NUCLEIC ACIDS

CROSS-REFERENCE TO RELATED APPLICATION

This application claims priority from Korean Patent Application No. 10-2008-0006793 filed on Jan. 22, 2008 in the Korean Intellectual Property Office, the disclosure of which is incorporated herein by reference in its entirety.

BACKGROUND

1. Field

The present invention relates to an apparatus for amplifying nucleic acids, and more particularly, to a nucleic acid amplifying apparatus having a uniform distribution of reaction temperature in a reaction space.

2. Description of the Related Art

In order to assay genetic information of nucleic acids such as DNA or RNA for base sequence analysis, medical diagnosis, and the like, amplification of trace amounts of nucleic acids in large quantities is required.

To this end, cell lysis, amplification of nucleic acids, or capillary electrophoresis (CE) may be performed. As nucleic acid amplification techniques well known in the art, there are a typical isothermal amplification technique, such as LCR (Ligase Chain Reaction), SDA (Strand Displacement Amplification), NASBA (Nucleic Acid Sequence-Based Amplification), or TMA (Transcription Mediated Amplification), and non-isothermal amplification techniques such as PCR (Polymerase Chain Reaction).

A typical non-isothermal amplification, PCR is performed by repeated cycles of thermal reactions: denaturation, annealing, and extension, which are to be performed in specific temperature ranges to acquire nucleic acids in high yields with great fidelity. In other words, it is preferable to maintain the reaction temperature in a constant range for both isothermal amplification and non-isothermal amplification.

Cell lysis is a process of disrupting cell membranes and releasing intracellular structures, for example, typically removal of DNA or RNA from the cell prior to amplification such as PCR. Cell lysis is largely performed using a mechanical or non-mechanical method. In particular, it is preferable to maintain a heating temperature during the non-mechanical method of disrupting many intracellular structures by heating cells.

Recently, there has been increasing demand for Lab-On-a-Chip (LOC) on which reactions such as cell lysis, nucleic acid amplification, and so on, are performed on a single microarray substrate. In a lab-on-a-chip (LOC), since nucleic acids are amplified in a tiny substrate, controlling a temperature of each reaction chamber for cell lysis or nucleic acid amplification influences analysis efficiency.

However, according to the distance from a heating unit, the number of heating units in the vicinity of each site, or the area occupied by the heating units, temperatures may vary at various sites of the reaction space or cell lysis space. In this case, different temperatures at various sites of the reaction space or cell lysis space may reduce the yield of nucleic acids or cause deterioration in the fidelity of the acquired nucleic acids.

SUMMARY

The present technology provides a nucleic acid amplifying apparatus having a substantially uniform distribution of reaction temperature in a reaction space. In one embodiment a nucleic acid amplification apparatus can be provided. The apparatus comprises a substrate providing a polymerase chain reaction space and a plurality of heating units disposed adjacent the reaction space to transfer heat to the reaction space. In an embodiment, the heating elements can be disposed above or below the outermost portions of the reaction space. In a further embodiment, the plurality of heating units can be arranged substantially in parallel with each other, and among the plurality of heating units. In still a further embodiment, the heating units can be disposed adjacent outermost portions of the reaction space having the largest heat radiation quantity. In another embodiment, the heating units can be conductive patterns. In still another embodiment, the conductive patterns can be disposed adjacent outermost portions of the reaction space having the largest area. In still another embodiment, the conductive patterns are disposed above or below the outermost portions.

In an embodiment herein the width of each of the conductive patterns disposed adjacent the outermost portions of the reaction space can be greater than innermost portions of the reaction space. In another embodiment herein the conductive patterns disposed adjacent outermost portions of the reaction space can be formed in a zigzag shape. In a further embodiment, the remaining conductive patterns are bar-shaped patterns having substantially the same width as the zigzag shaped patterns. In still a further embodiment, the heating units are disposed on a bottom surface of the substrate and transfer heat to the reaction space.

In an embodiment, the apparatus can further comprise a cover unit covering the reaction space and disposed above the substrate and a plurality of cooling units disposed on a bottom surface of the cover unit to eliminate heat from the reaction space. Further, the plurality of cooling units can be arranged substantially in parallel with each other, and the cooling units disposed adjacent outermost portions of the reaction space are capable of the largest amount of heat absorption. Moreover, the cooling units can be cooling coils, and the cooling coils disposed adjacent outermost portions of the reaction space are capable of the largest amount of heat absorption. The cooling coils can also be disposed above or below the outermost portions of the reaction space.

In a further embodiment the apparatus can comprise a cover unit covering the reaction space and disposed above the substrate, wherein the plurality of heating units can be disposed on a bottom surface of the cover unit to transfer heat to the reaction space. The apparatus can also comprise a plurality of cooling units disposed on a bottom surface of the substrate to eliminate heat from the reaction space. These plurality of cooling units can be arranged substantially parallel with each other, and the cooling units disposed adjacent outermost portions of the reaction space can be capable of the largest amount of heat absorption.

In one embodiment the apparatus can further comprise a cell lysis space formed on the substrate connected to the reaction space. In another embodiment, a preliminary heating unit can be disposed adjacent the cell lysis space to transfer heat to the cell lysis space. Moreover, the preliminary heating unit can be disposed above or below the cell lysis space. In still another embodiment, the preliminary heating unit can include a plurality of preliminary heating units arranged substantially parallel with each other. The preliminary heating units can be disposed adjacent outermost portions of the reaction space have the largest area. In a further embodiment, a preliminary cooling unit can be disposed adjacent to the cell lysis space so as to be spaced apart from the preliminary heating unit to eliminate heat from the cell lysis space, the cell lysis space passes through regions where the preliminary heating unit and the preliminary cooling unit are provided. Furthermore, the preliminary cooling unit can be disposed above or below the cell lysis space. In still a further embodiment, the preliminary heating unit includes a plurality of preliminary heating units arranged substantially in parallel with each other. In an additional embodiments, outermost preliminary heating units can have the largest area, and/or the preliminary cooling unit can include a plurality of preliminary cooling units arranged substantially in parallel with each other, and/or the outermost preliminary cooling units can have the largest area.

The apparatus can further comprise a heat insulation unit provided between a region where the preliminary heating unit is disposed and a region where the preliminary cooling unit is disposed. In another embodiment, the cell lysis space can include a first channel through which the sample flows from the preliminary heating unit to the preliminary cooling unit and/or a second channel through which the sample flows from the preliminary cooling unit to the preliminary heating unit, the first and second channels being connected to each other. In still another embodiment, the reaction space has an outlet side, an inlet channel and a central portion, the reaction space having a width gradually increasing from sides of the inlet channel, and from the outlet side to the central portion.

A particular arrangement of the nucleic acid amplification apparatus comprises a first substrate, a polymerase chain reaction space recessed within one surface of the substrate, an inlet channel formed on one surface of the substrate and connected to one end of the reaction space, an outlet channel formed on one surface of the substrate and connected to the other end of the reaction space, a conductive pattern disposed adjacent to the reaction space to transfer heat to the reaction space, and a second substrate disposed to cover the one surface of the substrate. Additionally, the conductive pattern can be disposed above or below the reaction space. In an embodiment herein, the conductive pattern can include a plurality of patterns arranged substantially in parallel with each other on the other surface of the first substrate, the conductive patterns being disposed at a connected portion of the reaction space. In still another embodiment, the inlet channel and a connected portion of the reaction space and the outlet channel have the largest width.

In an embodiment the apparatus can further comprise a cooling coil formed on the other surface of the second substrate for eliminating heat from the reaction space, the cooling coil including a plurality of coils disposed substantially in parallel with each other, the coils disposed adjacent a connected portion of the reaction space, in another embodiment above the connected portion. The coils can also be disposed above or below the connected portion of the reaction space. The inlet channel and a connected portion of the reaction space and the outlet channel can have the largest width. The apparatus can also further comprise a cell lysis space formed on one surface of the substrate between the reaction space and the inlet channel, a preliminary conductive pattern disposed adjacent the cell lysis space, and a connection channel formed on one surface of the first substrate connecting the cell lysis space with the reaction space. In one embodiment, the preliminary conductive pattern includes a plurality of conductive patterns disposed substantially in parallel with each other, the conductive patterns disposed at a connected portion of the reaction space and the inlet channel. A connected portion of the reaction space and the connection channel, can have the largest area. The apparatus can further comprise the cell lysis space, a plurality of preliminary conductive patterns arranged adjacent the cell lysis space substantially parallel with each other to transfer heat to the cell lysis space, a plurality of preliminary cooling coils arranged adjacent the cell lysis space substantially parallel with each other so as to be spaced apart from the preliminary conductive patterns and disposed at the outermost portions to eliminate heat from the cell lysis space, and a connection channel connecting the cell lysis space with the reaction space, wherein the preliminary conductive pattern or the preliminary cooling coil disposed at a connected portion of the cell lysis space. The inlet channel or a connected portion of the cell lysis space and the connection channel can have the largest area.

BRIEF DESCRIPTION OF THE DRAWINGS

The above and other features and advantages of the present invention will become more apparent by describing in detail preferred embodiments thereof with reference to the attached drawings in which.

DETAILED DESCRIPTION

Figure 1:
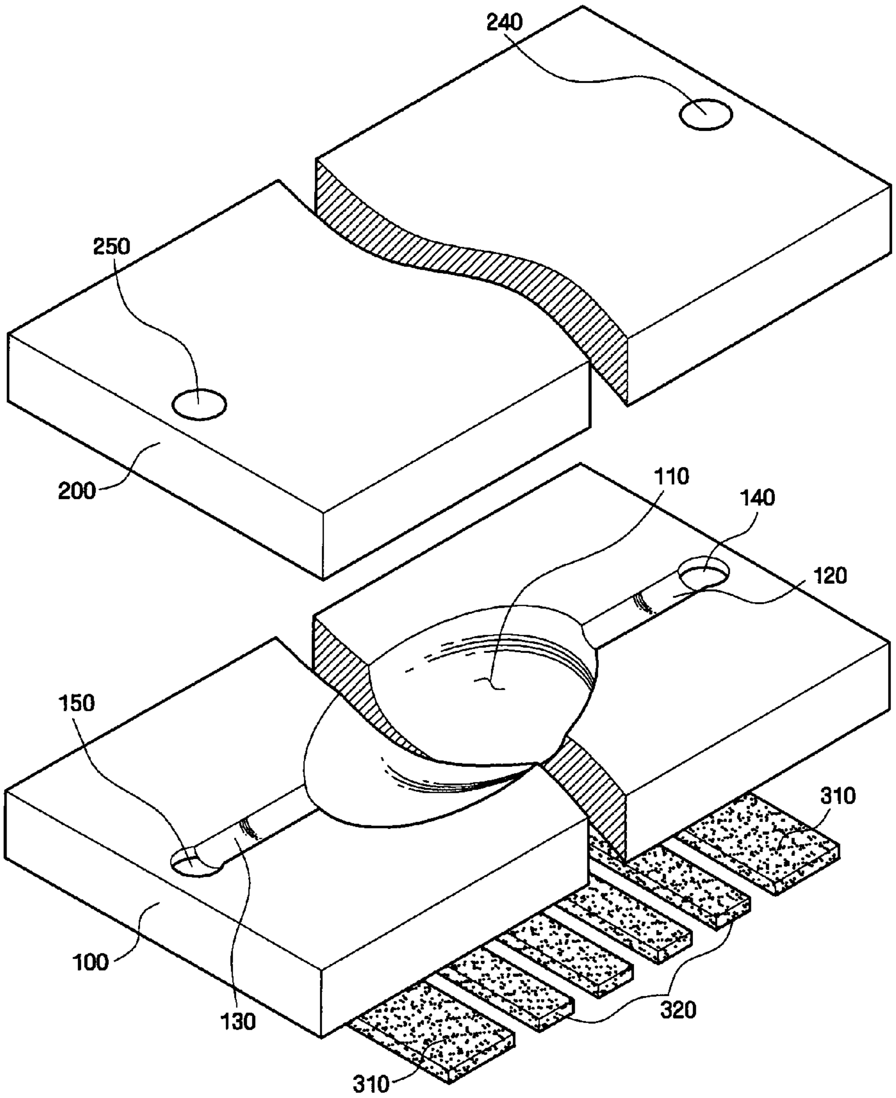
FIG. 1 is an exploded perspective view of a nucleic acid amplification apparatus according to a first embodiment.

Advantages and features of the present technology and methods of accomplishing the same may be understood more readily by reference to the following detailed description of preferred embodiments and the accompanying drawings. The present technology may, however, be embodied in many different forms and should not be construed as being limited to the embodiments set forth herein. Rather, these embodiments are provided so that this disclosure will be thorough and complete and will fully convey the concept of the technology to those skilled in the art, and the present technology will only be defined by the appended claims. Like reference numerals refer to like elements throughout the specification.

It will be understood that although the terms used herein are used to describe exemplary embodiments, the technology should not be limited by these terms. It will be further understood that the terms “comprises” and/or “comprising” when used in this specification, specify the presence of stated features, regions, integers, steps, operations, elements, and/or components, but do not preclude the presence or addition of one or more other features, regions, integers, steps, operations, elements, components, and/or groups thereof.

Figure 2:
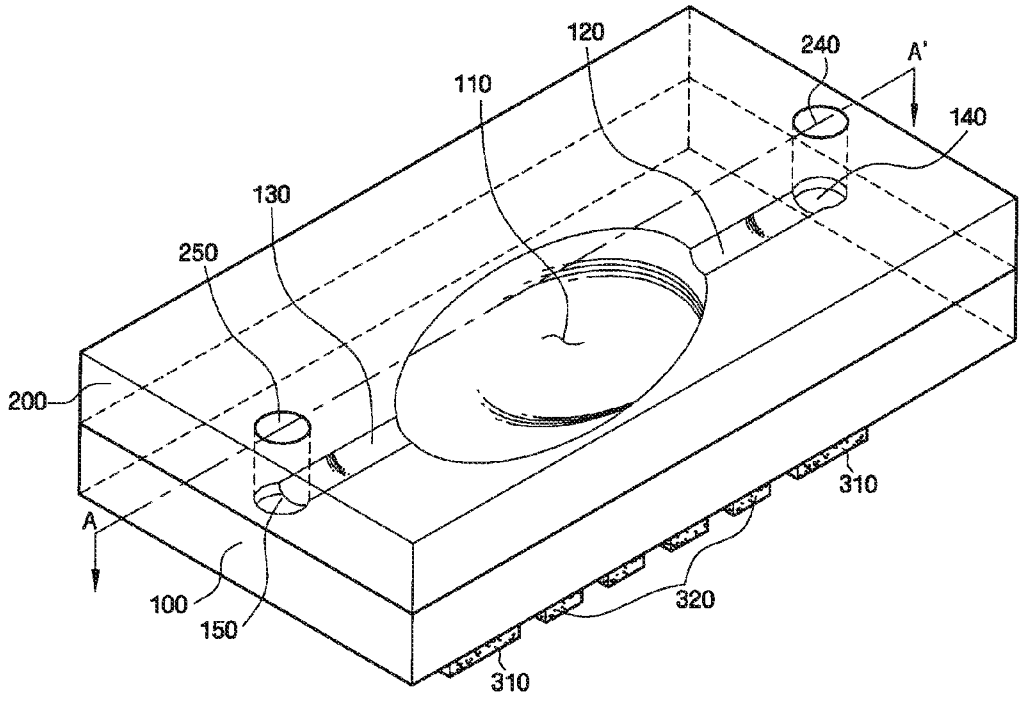
FIG. 2 is a perspective view of the nucleic acid amplification apparatus shown in FIG. 1.
Figure 3:
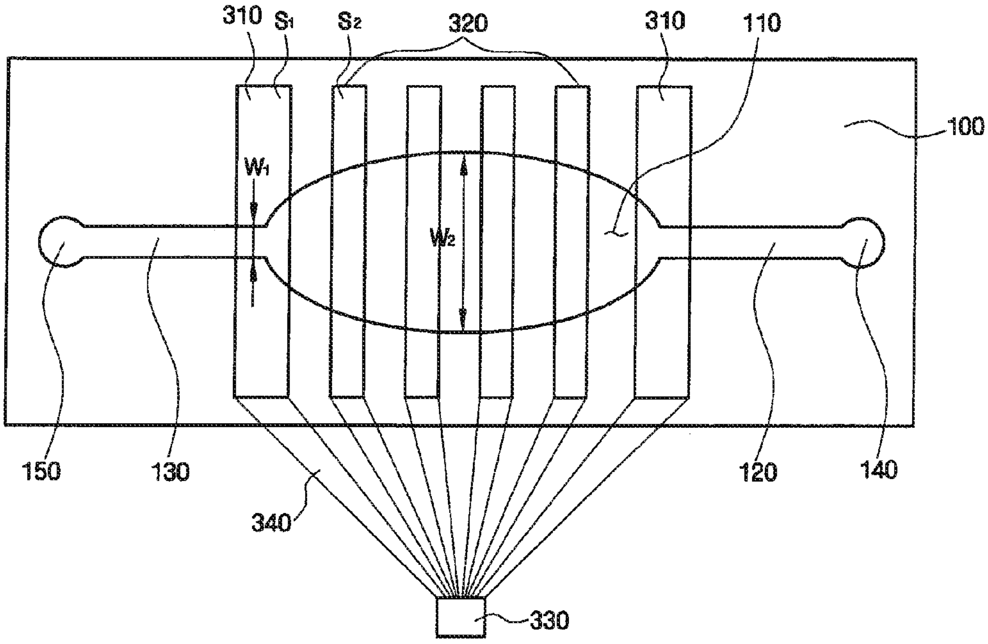
FIG. 3 is a front view of the nucleic acid amplification apparatus shown in FIG. 1.

FIG. 1 is an exploded perspective view of a nucleic acid amplification apparatus according to a first embodiment, FIG. 2 is a perspective view of the nucleic acid amplification apparatus shown in FIG. 1, and FIG. 3 is a front view of the nucleic acid amplification apparatus shown in FIG. 1.

Referring to FIGS. 1 through 3, the nucleic acid amplification apparatus includes a substrate 100 providing a PCR space 110 and a cover unit 200. Throughout this specification, the substrate 100 and the cover unit 200 are also referred to as a first substrate and a second substrate. Unless specifically defined, the substrate 100 means the first substrate. The PCR space 110 is also referred to as a reaction space.

The substrate 100 is made of a material having rigidity and excellent processability. To allow various reactions occurring in the reaction space 110 to be identified, the substrate 100 is, in one embodiment, optically transparent.

In detail, the substrate 100 may be made of silicon, glass such as soda lime glass or boro-silicate glass, a polymer or copolymer comprising one of COC (Cyclo Olefin Copolymer), PMMA (PolyMethylMethAcrylate), PC (PolyCarbonate), COP (Cyclo Olefin Polymer), LCP (Liquid Crystalline Polymers), PDMS (PolyDiMethylSiloxane), PA (PolyAmide), PE (PolyEthylene), PI (PolyImide), PP (PolyPropylene), PPE (PolyPhenylene Ether), PS (PolyStyrene), POM (PolyOxyMethylene), PEEK (PolyEtherEtherKetone), PET (PolyEthylenephThalate), PTFE (PolyTetraFluoroEthylene), PVC (PolyVinylChloride), PVDF (PolyVinyliDeneFluoride), PBT (PolyButyleneTerephthalate), FEP (Fluorinated Ethylene Propylene), and PFA (PerFluorAlkoxyalkane).

The substrate 100 may be manufactured by injection molding using a mold processed with CMP (Chemical Mechanical Polishing), extrusion molding, hot embossing or casting, stereolithography, laser ablation, rapid prototyping, casting, silk screening, machining such as NC (Numerical Control) machining, or a semiconductor fabrication technique such as photolithography.

The reaction space 110 is formed on one surface of the substrate 100. The reaction space 110 is recessed from the one surface of the substrate 100.

The reaction space 110 is connected to an inlet channel 120, allowing introduction of nucleic acids, and an outlet channel 130, releasing the amplified nucleic acids. A width $w_1$ of an outermost portion of the reaction space 110, corresponding to a connected portion of the reaction space 110 and the inlet channel 120 and a connected portion of the reaction space 110 and the outlet channel 130, may be smaller than a width $w_2$ of a central portion of the reaction space 110. In more detail, the width of the reaction space 110 may gradually increase from its outermost portion to its central portion. In this case, nucleic acids transferred from the inlet channel 120 to the reaction space 110 are distributed throughout the reaction space 110, so that in one embodiment a substantially minimum void volume, and in another embodiment substantially no void volume, exists in the reaction space 110. In this way, in an embodiment herein, substantially most of the volume of the reaction space 110, and in a further embodiment substantially the entire volume of the reaction space 110, can be employed as an effective area for reactions. The reaction space 110 may have various shapes including a cube, a rectangular parallelepiped, a hemispherical, or an elliptical shape, as long as it allows the volume of the reaction space 110 to be efficiently utilized. In one embodiment, the reaction space 110 may be formed by etching the substrate 100 made of glass or silicon or performing injection molding a plastic substrate. The reaction space 110 may be formed at the same time with the inlet channel 120 and the outlet channel 130 or separately from other processing units.

While in one embodiment the reaction space 110 may be provided to have a dimension in a range of about 200 to about 500 nL, the size of the reaction space 110 is not limited to this specific range.

The inlet channel 120 and the outlet channel 130 each having a small width are formed on the substrate 100. Nucleic acids are transferred to a first end of the reaction space 110 through the inlet channel 120 and the amplified nucleic acids are discharged to a second end of the reaction space 110 through the outlet channel 130. In a case where only a PCR process is performed on the substrate 100, the reaction space 110 is directly connected to one end of the inlet channel 120 and an inlet well 140 is connected to the other end of the inlet channel 120 to allow introduction of nucleic acids. However, in a case where prior to the PCR process, a cell lysis process should be performed on the substrate 100, a cell lysis space (not shown) may be connected to the inlet channel 120. Likewise, in a case where only the PCR process is performed on the substrate 100, the reaction space 110 is directly connected to one end of the outlet channel 130 and the inlet well 140 is connected to the other end of the outlet channel 130. Meanwhile, in a case where not only the PCR process but also a microfluidic electrophoresis should be performed on the substrate 100, the outlet channel 130 may be connected to a microfluidic electrophoresis space (not shown). A valve (not shown) may be provided at each of the inlet channel 120 and the outlet channel 130 to control the flow of nucleic acids.

The cover unit 200 covering the reaction space 110 is disposed above the substrate 100. The cover unit 200 prevents foreign substances contained in the reaction space 110, the inlet channel 120, and the outlet channel 130 from being introduced into the nucleic acids.

The cover unit 200 may be made of the same material as the substrate 100. In one embodiment, the reaction space 110 is optically transparent so as to be observed from the outside.

The cover unit 200 may be provided with an inlet port 240 allowing introduction of a sample, such as nucleic acids, and an outlet port 250 used to remove the sample. The inlet port 240 and the outlet port 250 may be disposed at a lower portion of the substrate 100.

The inlet port 240 may be formed directly above the inlet well 140. The sample of nucleic acids introduced into the inlet port 240 is supplied to the reaction space 110 through the inlet well 140 and the inlet channel 120 may vary but are, in one embodiment located toward the outer ends of substrate 100.

The outlet port 250 may be formed directly above the outlet well 150. The amplified nucleic acids supplied from the reaction space 110 are discharged to the outlet port 250 through the outlet channel 130 and the outlet well 150. In an embodiment, potential energy providing means, e.g., a pump, may be utilized.

The substrate 100 and the cover unit 200 may be thermally isolated using a material having low thermal conductivity, e.g., a polymer film. This should increase heating and cooling speeds.

The substrate 100 and the cover unit 200 may be bonded to each other using coupling means or a bonding material. A liquid-type adhesive material, a powder-type adhesive material, or an adhesive material of a thin plate type, such as paper, can be used as the bonding material. In order to prevent biochemical substance from being degraded during bonding, room-temperature bonding or low-temperature bonding may be necessarily performed. In such a case, bonding may be performed by means of a pressure sensitive adhesive using only pressure or by ultrasonic bonding in which a substrate is locally melted using ultrasonic energy. In this case, it is necessary to prevent a nucleic acid sample from being leaked to the outside or foreign matter from being introduced from the outside through crevices created between the cover unit 200 and the substrate 100.

The nucleic acid amplification apparatus according to the first embodiment amplifies nucleic acids released from cells. In the following description, the nucleic acid amplification apparatus according to the first embodiment will be explained in detail with regard to a PCR apparatus amplifying DNAs (DeoxyriboNucleic Acids) by way of example.

The PCR is performed by repeated cycles of three steps: denaturation, annealing, and extension. In the denaturation step, a double-stranded DNA can be separated in one embodiment into two single strands by heating at a temperature of at least about 90° C., and in another embodiment at a temperature of at least about 95° C. In the annealing step, two primers are each bound to the complementary opposite strands in one embodiment at an annealing temperature of from about 50 to 60° C., and in another embodiment at 52° C., for from about 30 seconds to about several minutes. In the extension step, DNA polymerase initiates extension at the ends of the hybridized primers to obtain DNA double strands. The time required for the extension step varies depending on the concentration of a template DNA, the size of an amplification fragment, and an extension temperature. In the case of using common Thermusaquaticus (Taq) polymerase, the primer extension is performed at about 72° C. for from about 30 seconds to about several minutes.

As described above, the yield of the PCR process is highly dependant upon the temperature, a substantially uniform temperature profile should be maintained throughout the reaction space 110 and the temperature of the reaction space 110 should be controlled as well.

In the current embodiment, heating units 310 and 320 are disposed at a position corresponding to the reaction space 110, for example, below the reaction space 110, so as to transfer heat to the reaction space 110.

Figure 4:
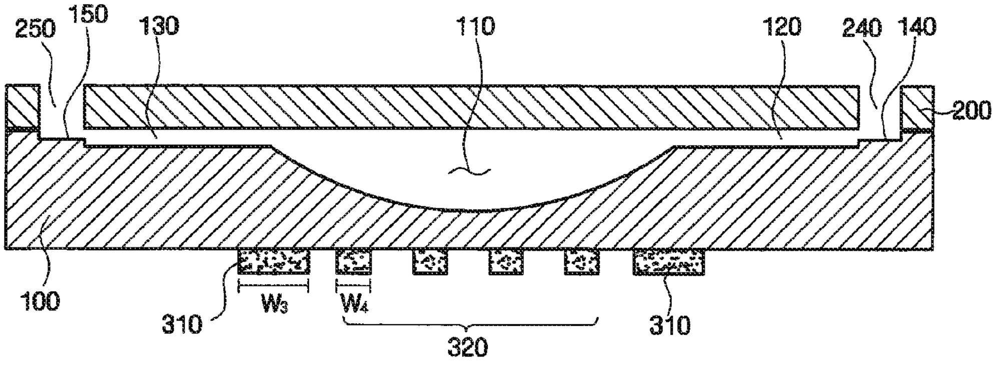
FIG. 4 is a cross-sectional view taken along line A-A' of FIG. 2.

Hereinafter, the heating units according to the current embodiment of the present invention will be described in detail with reference to FIGS. 1 through 4. FIG. 4 is a cross-sectional view of the nucleic acid amplification apparatus according to the first embodiment of the present invention, taken along line A-A' of FIG. 2.

Referring to FIGS. 1 through 4, a plurality of heating units 310 and 320 may be disposed below the reaction space 110. The heating units 310 and 320 may have a shape that can facilitate heat transfer, in one embodiment, a bar shape. The plurality of heating units 310 and 320 may be arranged in parallel with each other or may be separated from each other. In order to improve uniformity in the heat distribution in the reaction space 110, the heating units 310 and 320 may in an embodiment herein be spaced apart from each other at substantially equal spacing.

The heating units 310 and 320 include first heating units 310 and second heating units 320. The first heating units 310 are disposed at the outermost portions of the reaction space 110, that is, below a connected portion of the reaction space 110 and the inlet channel 120 and a connected portion of the reaction space 110 and the outlet channel 130, respectively. The second heating units 320 are disposed between the outermost first heating units 310 that are positioned at opposite ends of the reaction space 110.

Since heat is emitted in a radial direction from the first and second heating units 310 and 320 and the first and second heating units 320 are spaced apart from each other, in one embodiment at substantially equal spacing, heat distribution is uniform at a central portion of the reaction space 110. In the current embodiment, the heating units are arranged such that the first heating units 310 disposed at the outermost portions of the reaction space 110 have the largest heat radiation quantity. That is to say, when the second heating units 320 have the same heat radiation quantity, the first heating units 310 are designed to have a larger heat radiation quantity than the second heating units 320. Heating units other than the first heating units 310, i.e., the second heating units 320, exist only at one side of the first heating units 310, and no other heating units (not shown) exist at the other side of the first heating units 310. Accordingly, as in a further embodiment, heat radiation quantities of the first heating units 310 and the second heating units 320 are substantially equal, the outermost portions of the reaction space 110 may be a lower temperature distribution than the central portion of the reaction space 110. Like in the current embodiment, however, the heat radiation quantities of the first heating units 310 are made to be larger than those of the second heating units 320, thereby preventing nonuniformity in the temperature distribution of the reaction space 110.

The heating units 310 and 320 of the current embodiment may be, for example, conductive patterns. The conductive patterns may be made of various kinds of metals such as Pt, Ag, Al, or Cu, metallic oxides such as RuO2, or doped polysilicon. The conductive patterns may be fabricated by a semiconductor processing technique using photolithography and etching, laser ablation, screen printing, or electroplating.

First, in a case of the heating units 310 and 320 fabricated as conductive patterns using photolithography, a conductive material can be coated on a bottom surface of the substrate 100, which is opposite to a substrate surface where the reaction space is formed and is also referred to as a rear surface of the substrate, to a uniform thickness. Thereafter, patterned photoresist is formed and the conductive material is then etched away for removal, thereby completing the heating units 310 and 320. In this case, shapes of the photoresist patterns are adjusted such that an area $S_1$ of each of the first heating units 310 becomes greater than an area $S_2$ of each of the second heating units 320. In detail, a width $w_3$ of each of the first heating units 310 is made to be greater than a width $w_4$ of each of the second heating units 320 by adjusting widths of the photoresist patterns, thereby making the heat radiation quantities of the first heating units 310 larger than the heat radiation quantities of the second heating units 320. Accordingly, it is possible to prevent a temperature distribution at the outermost first heating units 310 from being lower than that at the central portion of the reaction space 110, so that the temperatures become uniformly distributed over the entire area of the reaction space 110.

Meanwhile, a heat controlling unit 330 controls heat to be transferred to the heating units 310 and 320 through heating unit transfer units 340 connected to the heating units 310 and 320. The heat controlling unit 330 may be, for example, a switch, and converts electric energy into heat energy to be supplied to the heating units 310 and 320.

Hereinafter, an exemplary method of conducting PCR on DNAs using the nucleic acid amplification apparatus according to a current embodiment will be described.

First, a reactant solution containing a mixture including template DNAs, a DNA polymerase, and primers is prepared. For example, the reactant solution may include 1.0 μl of a PCR buffer solution, 1.04 μl of distilled water, 0.1 μl of 10 mM dNTPs, 0.2 μl of 20 μM of a primer mixture, and 0.16 μl of a polymerase mixture. DNAs and the solution are mixed in a ratio of 1:1 by volume, to then be fed to the nucleic acid amplification apparatus according to the current embodiment. In this case, the DNAs may be released from cells after a cell lysis process.

The reactant solution may be introduced through the inlet port 240 of the cover unit 200. The reactant solution is supplied to the reaction space 110 through the inlet well 140 and the inlet channel 120 of the substrate 100. When the reaction space 110 is supplied with the reactant solution, the heat controlling unit 330 is turned on to apply heat to the heating units 310 and 320 to then heat the reaction space 110 until the temperature of the reaction space 110 reaches 95° C. Thereafter, the reaction space 110 is cooled to attach primers to template DNAs, followed by annealing. In this case, the cooling of the reaction space 110 may be performed using a separate cooling unit. Alternatively, the reaction space 110 may be naturally cooled using ambient air. Further, heat may be transferred to the reaction space 110 using the heating units 310 and 320, thereby allowing the reaction space 110 to be maintained at a temperature required to perform an annealing process for a predetermined period of time. Next, the primers are subjected to extension using, for example, a Taq polymerase, for amplifying DNAs. Here, the temperature of the reaction space 110 is elevated using the heating units 310 and 320 to then maintain the reaction space 110 at 72° C. The above-described reaction cycles are performed repeatedly, for example, 30 cycles, to amplify the DNAs.

While the repeated cycles of reactions including denaturation, annealing, and extension are in-situ performed in a single reaction space 110 in the current embodiment, the technology is not limited to the exemplary embodiment, the denaturation, annealing, and in another embodiment extension reactions may be separately performed in three independent reaction spaces (not shown) using separate heating units (not shown).

In the nucleic acid amplification apparatus according to the current embodiment, the temperature of the reaction space 110 can be accurately controlled with uniformity throughout the reaction space 110, thereby efficiently performing the PCR process.

Figure 5:
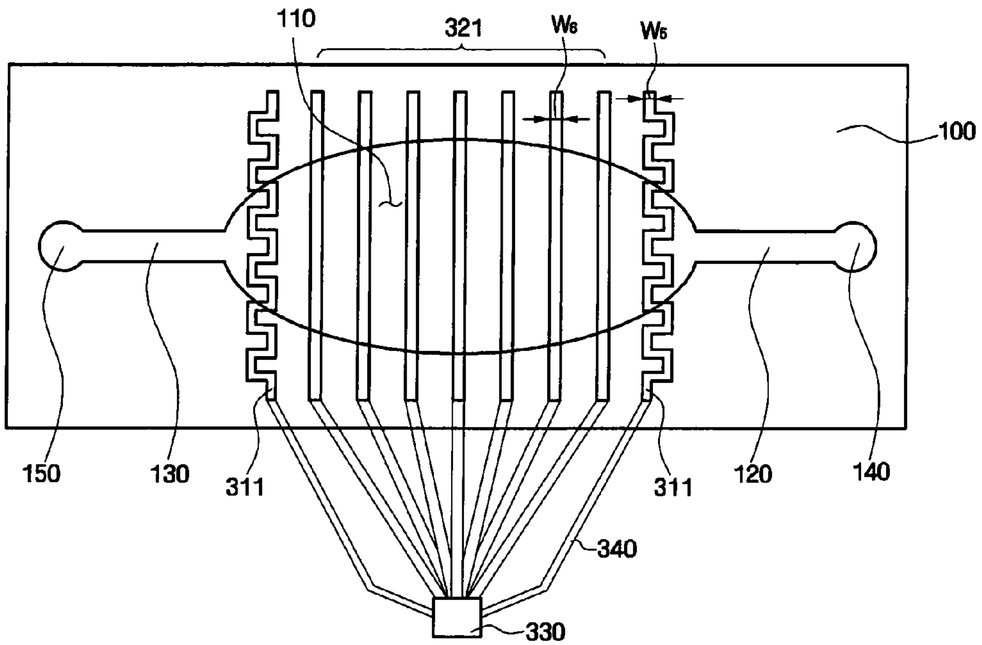
FIG. 5 is a front view of a nucleic acid amplification apparatus according to a second embodiment.

Hereinafter, a nucleic acid amplification apparatus according to a second embodiment of the present invention will be described in detail with reference to FIG. 5. FIG. 5 is a front view of a nucleic acid amplification apparatus according to a second embodiment of the present invention. For brevity, in the following embodiments, detailed descriptions of the same elements as those of the first embodiment will not be given or will be briefly given.

Referring to FIG. 5, heating units 311 and 321 of that embodiment may be disposed below a reaction space 110. The first heating units 311 may be formed as conductive patterns, for example, and patterned in a substantially zigzag shape. The other heating units, i.e., the second heating units 321, may in one embodiment be bar-shaped conductive patterns, like in the previous embodiment. A width $w_5$ of each of the first heating units 311 in one embodiment can be substantially the same as a width $w_6$ of each of the second heating units 321.

Since the first heating units 311 are patterned in a substantially zigzag shape, areas of the first heating units 311 facing the reaction space 110 are in that embodiment greater than areas of the second heating units 321, so that heat radiation quantities of the first heating units 311 become substantially larger than those of the second heating units 321. Accordingly, the temperature distribution at the outermost portions of the reaction space 110 is substantially the same as the temperature distribution at the central portion of the reaction space 110, thereby efficiently performing PCR.

Figure 6:
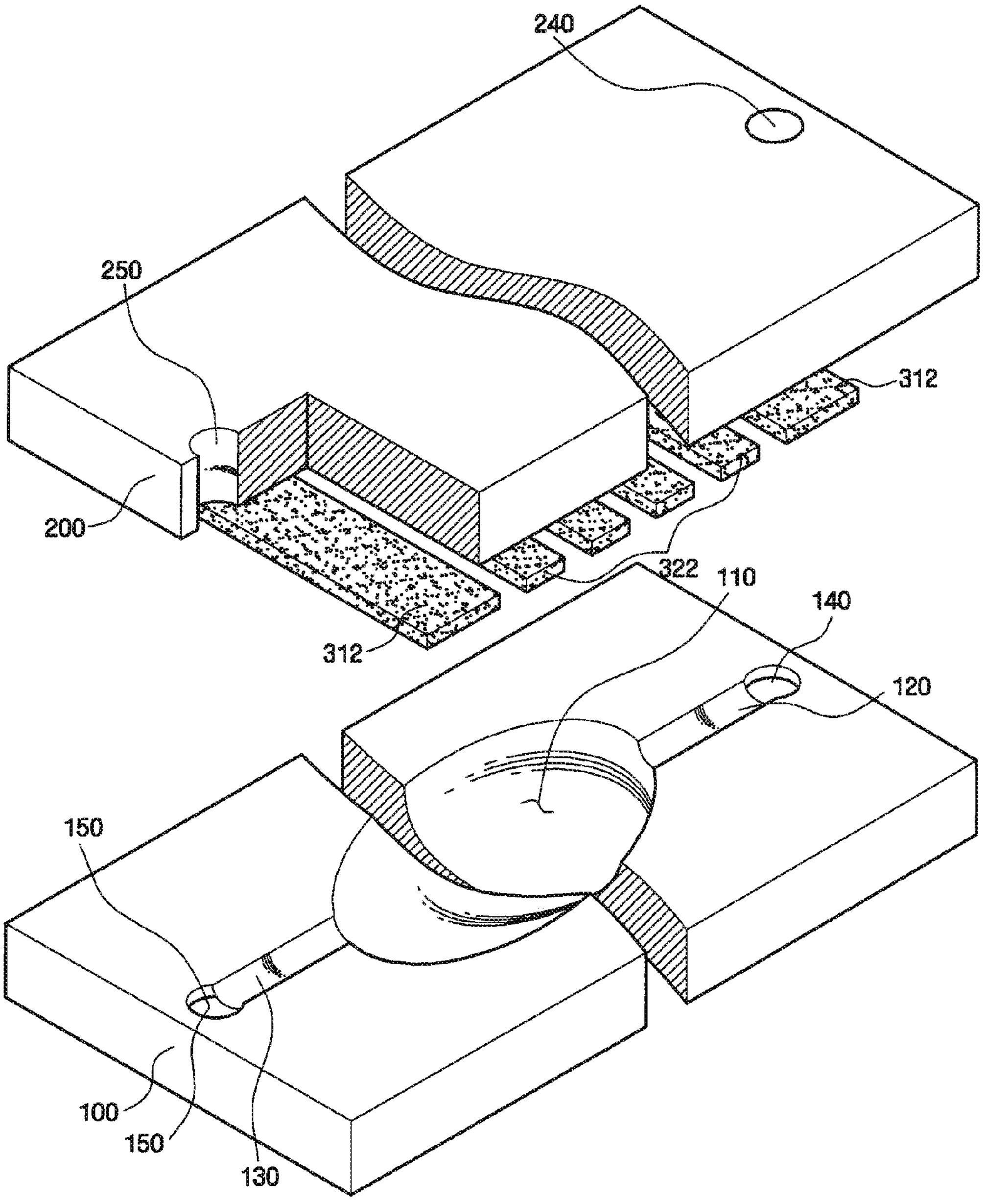
FIG. 6 is an exploded perspective view of a nucleic acid amplification apparatus according to a third embodiment.
Figure 7:
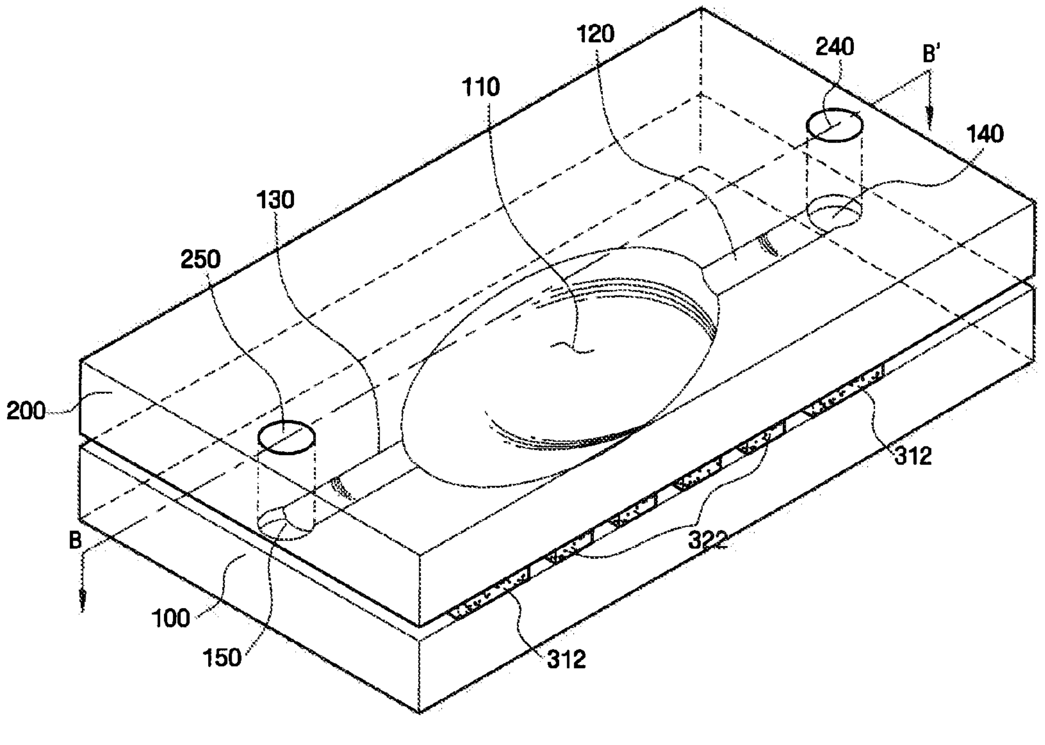
FIG. 7 is a perspective view of the nucleic acid amplification apparatus shown in FIG. 6.
Figure 8:
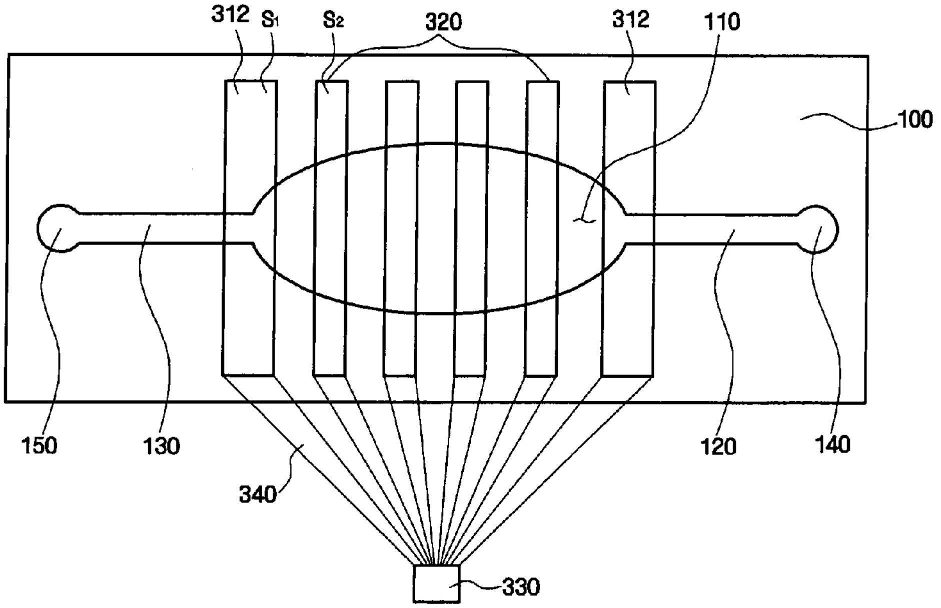
FIG. 8 is a front view of the nucleic acid amplification apparatus shown in FIG. 6.
Figure 9:
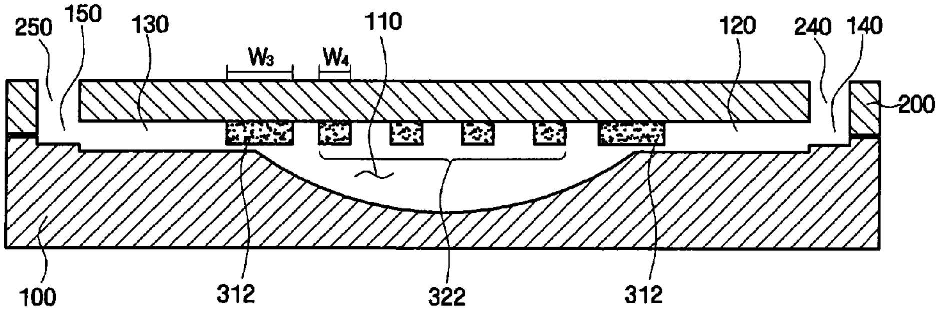
FIG. 9 is a cross-sectional view taken along line B-B' of FIG. 7.

Hereinafter, a nucleic acid amplification apparatus according to a third embodiment of the present invention will be described in detail with reference to FIGS. 6 through 9. FIG. 6 is an exploded perspective view of a nucleic acid amplification apparatus according to a third embodiment of the present invention, FIG. 7 is a perspective view of the nucleic acid amplification apparatus shown in FIG. 6, FIG. 8 is a front view of the nucleic acid amplification apparatus shown in FIG. 6, and FIG. 9 is a cross-sectional view taken along line B-B' of FIG. 7.

Referring to FIGS. 6 through 9, the nucleic acid amplification apparatus according to the current embodiment of the present invention includes heating units 312 and 322 formed at a cover unit 200. The heating units 312 and 322 are formed above a reaction space 110, more specifically on a bottom surface of the cover unit 200 and transfer heat to the reaction space 110.

Since the heating units 312 and 322 are formed at the cover unit 200, they become closer to a nucleic acid sample, thereby easily controlling the temperature of the reaction space 110.

A method of forming the heating units 312 and 322 on the bottom surface of the cover unit 200 is substantially the same as described above in the first embodiment, except that the heating units 312 and 322 are covered with insulation films (not shown) to prevent the nucleic acid sample from contacting a reactant solution.

Figure 10:
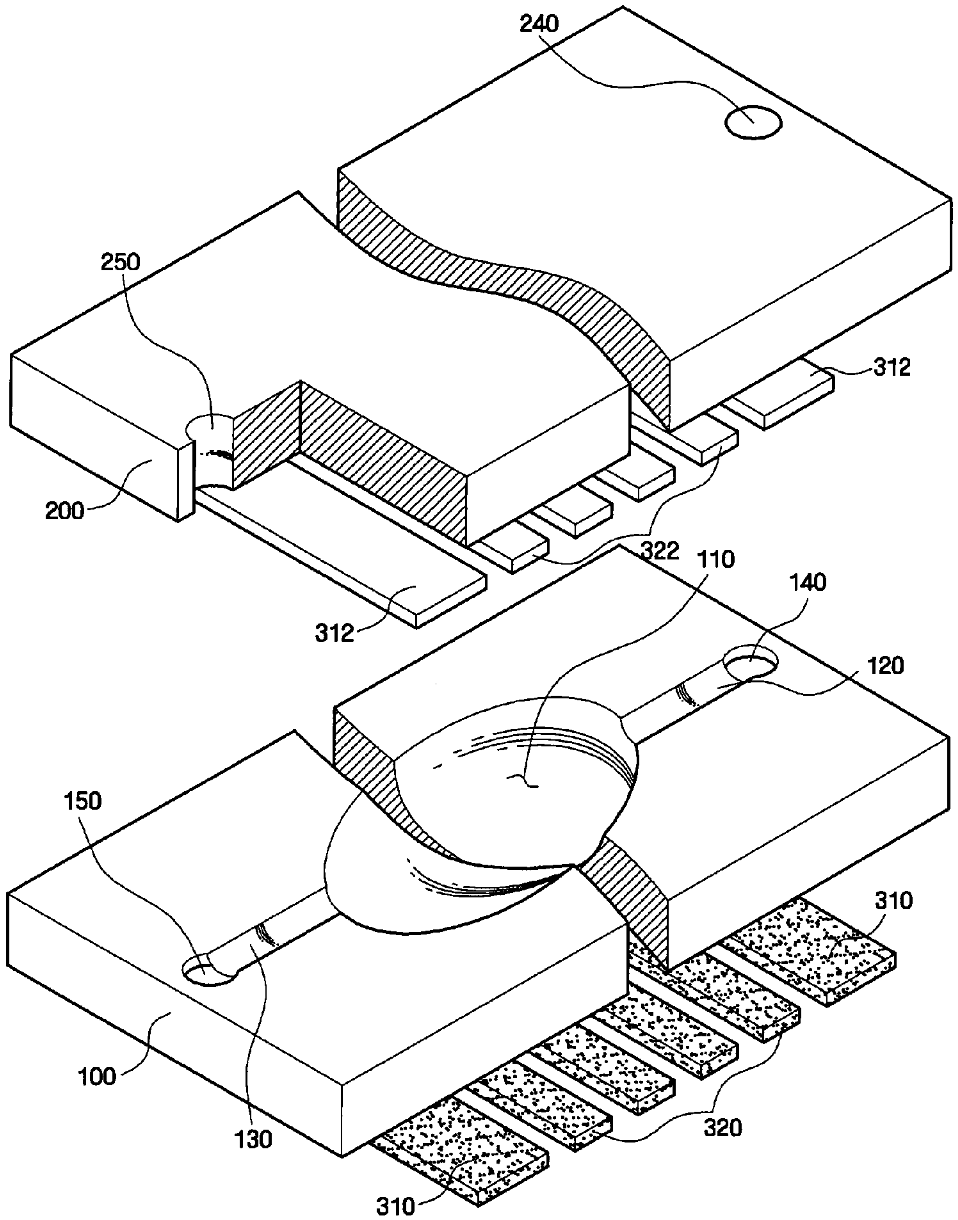
FIG. 10 is an exploded perspective view of a nucleic acid amplification apparatus according to a fourth embodiment.
Figure 11:
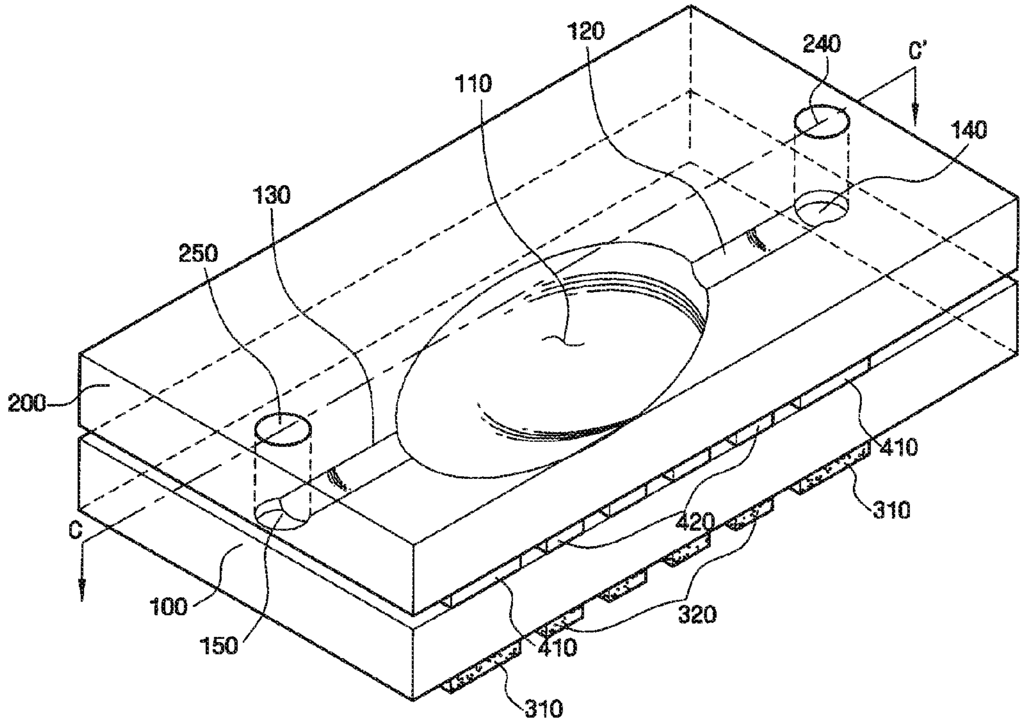
FIG. 11 is a perspective view of the nucleic acid amplification apparatus shown in FIG. 10.
Figure 12:
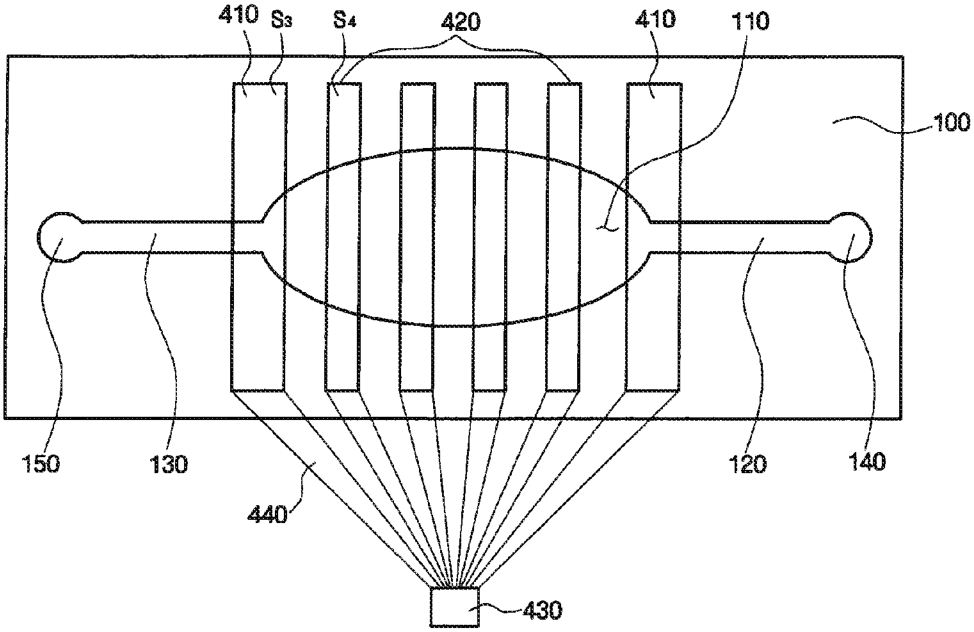
FIG. 12 is a front view of the nucleic acid amplification apparatus shown in FIG. 10.
Figure 13:
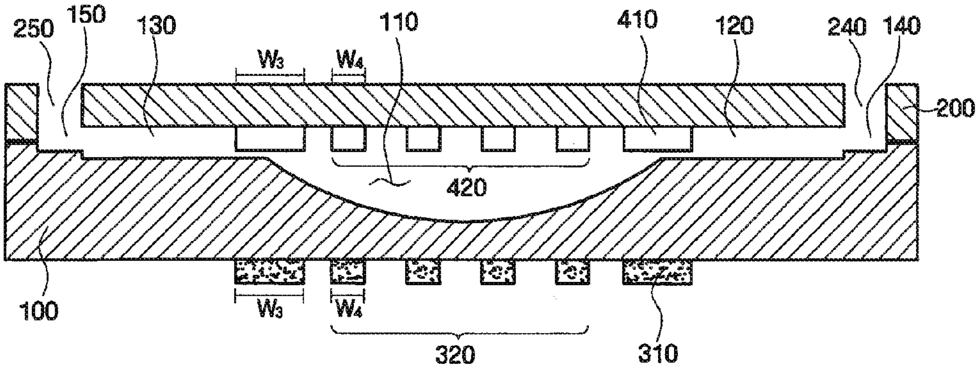
FIG. 13 is a cross-sectional view taken along line C-C' of FIG. 11.

Hereinafter, a nucleic acid amplification apparatus according to a fourth embodiment of the present invention will be described in detail with reference to FIGS. 10 through 13. FIG. 10 is an exploded perspective view of a nucleic acid amplification apparatus according to a fourth embodiment of the present invention, FIG. 11 is a perspective view of the nucleic acid amplification apparatus shown in FIG. 10, FIG. 12 is a front view of the nucleic acid amplification apparatus shown in FIG. 10, and FIG. 13 is a cross-sectional view taken along line C-C' of FIG. 11.

Referring to FIGS. 10 through 13, the nucleic acid amplification apparatus according to the current embodiment of the present invention is substantially the same as the nucleic acid amplification apparatus according to the first embodiment of the present invention, except that cooling units 410 and 420 are further provided below a cover unit 200.

Specifically, the nucleic acid amplification apparatus according to the current embodiment includes heating units 310 and 320 disposed below a substrate 100, and cooling units 410 and 420 disposed below the cover unit 200.

The cooling units 410 and 420 formed on a bottom surface of the cover unit 200 eliminate heat from the reaction space 110.

The cooling units 410 and 420 may include a plurality of first cooling units 410 and a plurality of second cooling units 420, respectively, which are arranged substantially in parallel with each other. The first cooling units 410 are disposed at the outermost portions of the reaction space 110, and heat absorption quantities of the first cooling units 410 are in this embodiment larger than those of the second cooling units 420. An area $S_3$ of each of the first cooling units 410 may be greater than an area $S_4$ of each of the second cooling units 420. The cooling units 410 and 420 may be bar-shaped, and a width $w_7$ of each of the first cooling units 410 is greater than a width $w_8$ of each of the second cooling units 420.

The cooling units 410 and 420 according to the current embodiment of the present invention may be cooling coils. As the cooling units 410 and 420 according to the current embodiment of the present invention, additional cooling devices, such as a cooling fan or a peltier device, may also be used.

In a case of using cooling coils as the cooling units 410 and 420, widths $w_7$ and $w_8$ of the cooling units 410 and 420 correspond to diameters of the cooling coils.

In order to prevent the cooling units 410 and 420 from contacting with a nucleic acid reactant solution, upper portions of the cooling units 410 and 420 may be coated with insulation films (not shown).

Meanwhile, a cooling source controlling unit 430 controls a cooling source to be transferred to the cooling units 410 and 420 through cooling source transfer units 440 connected to the cooling units 410.

Although not shown, the cooling units 410 and 420 may be disposed on a bottom surface of the substrate 100 and the heating units 310 and 320 may be disposed on the bottom surface of the cover unit 200. That is to say, positions of the cooling units 410 and 420 may be interchanged with positions of the heating units 310 and 320.

Figure 14:
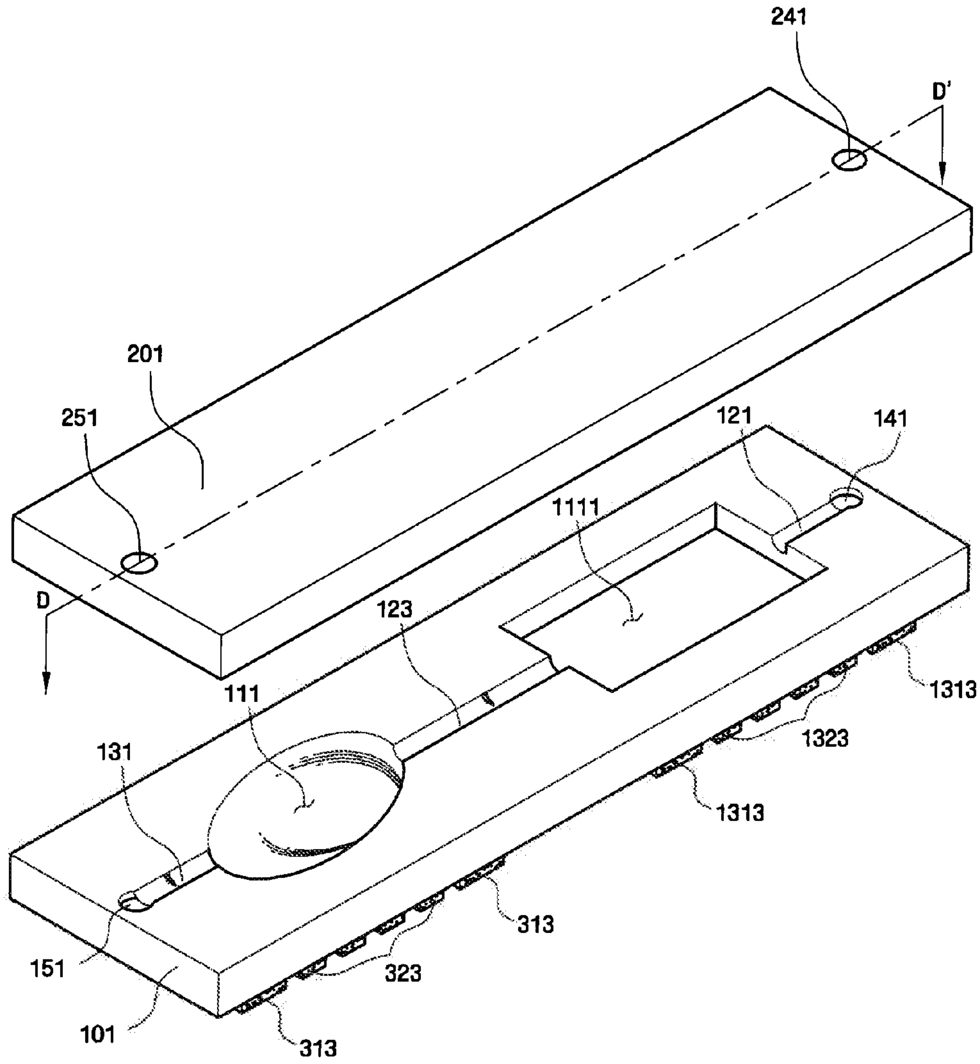
FIG. 14 is an exploded perspective view of a nucleic acid amplification apparatus according to a fifth embodiment.

Hereinafter, a nucleic acid amplification apparatus according to a third embodiment of the present invention will be described in detail with reference to FIGS. 14 and 15. FIG. 14 is an exploded perspective view of a nucleic acid amplification apparatus according to a fifth embodiment of the present invention, and FIG. 15 is a cross-sectional view taken along line D-D' of FIG. 14.

Figure 15:
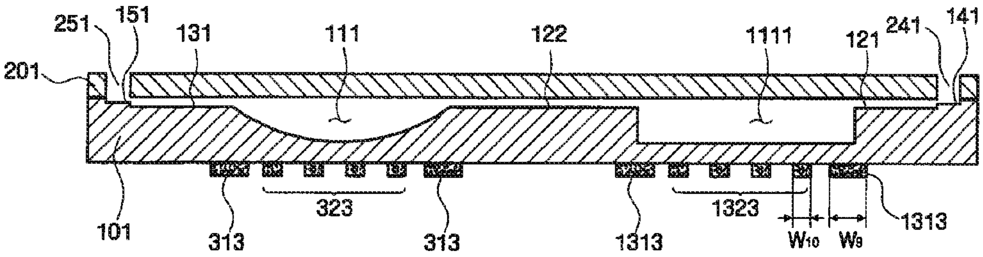
FIG. 15 is a cross-sectional view taken along line D-D' of FIG. 14.

Referring to FIGS. 14 and 15, the nucleic acid amplification apparatus is different from the nucleic acid amplification apparatuses according to the previous embodiments in that it further includes a cell lysis space 1111.

Cell lysis is a process of disrupting cell membranes and releasing intracellular structures. Cell lysis is typically performed to remove intracellular structures, for example, nucleic acids such as DNA or RNA, from the cell, prior to amplification such as PCR.

In the current embodiment, cells are introduced into the cell lysis space 1111 to release nucleic acids from the cell, and the released nucleic acids are transferred to the reaction space 111 for amplification.

In the cell lysis space 1111 according to the current embodiment, cells are heated to be released. The cell lysis space 1111 is recessed from the one surface of a substrate 101 and connected to the reaction space 111. The cell lysis space 1111 may have any kind of shape and the shape of the cell lysis space 1111 may be the same as or different from that of the reaction space 111.

One end of the cell lysis space 1111 is connected to an inlet channel 121 and the other end of the cell lysis space 1111 is connected to a connection channel 122, which is connected to the reaction space 111.

The cell lysis space 1111 is heated by preliminary heating units 1313 and 1323. The preliminary heating units 1313 and 1323 may be disposed above or below the cell lysis space 1111. Specifically, the preliminary heating units 1313 and 1323 may be formed on a bottom surface of the substrate 101. Although not shown, the preliminary heating units 1313 and 1323 may be formed on a bottom surface of a cover unit 201.

The preliminary heating units 1313 and 1323 may include a plurality of preliminary heating units. In this case, the preliminary heating units 1313 and 1323 may be arranged substantially in parallel with each other. In order to improve uniformity in heat distribution in the cell lysis space 1111, the preliminary heating units 1313 and 1323 may be arranged such that the first preliminary heating units 1313 disposed at the outermost portions of the cell lysis space 1111 have the largest heat radiation quantity.

An area of each of the outermost first preliminary heating units 1313, which are disposed at a connected portion of the cell lysis space 1111 and the inlet channel 121 and a connected portion of the cell lysis space 1111 and the connection channel 122, may be greater than an area of each of the second preliminary heating units 1323, which are disposed at a central portion of the cell lysis space 1111. In addition, a width w9 of each of the first preliminary heating units 1313 is made to be greater than a width w10 of each of the second preliminary heating units 1323.

The nucleic acid amplification apparatus according to the current embodiment operates in the following manner. A cell mixture introduced throughout an inlet port 241 of the cover unit 201 is transferred to the cell lysis space 1111 via an inlet well 141 and the inlet channel 121. In the cell lysis space 1111, intracellular structures, e.g., DNAs, are released using the preliminary heating units 1313 and 1323. The released DNAs are introduced into the reaction space 111 through the connection channel 122 together with other mixtures to then be amplified. Next, the amplified DNAs are subjected to reactions occurring in another space of an LOC, e.g., a space for a microfluidic electrophoresis, through an outlet channel, and then discharged through an outlet well 151 and an outlet port 251.

The nucleic acid amplification apparatus according to the current embodiment can perform cell lysis and nucleic acid amplification on a single substrate, thereby readily achieving temperature control during the cell lysis and nucleic acid amplification.

Figure 16:
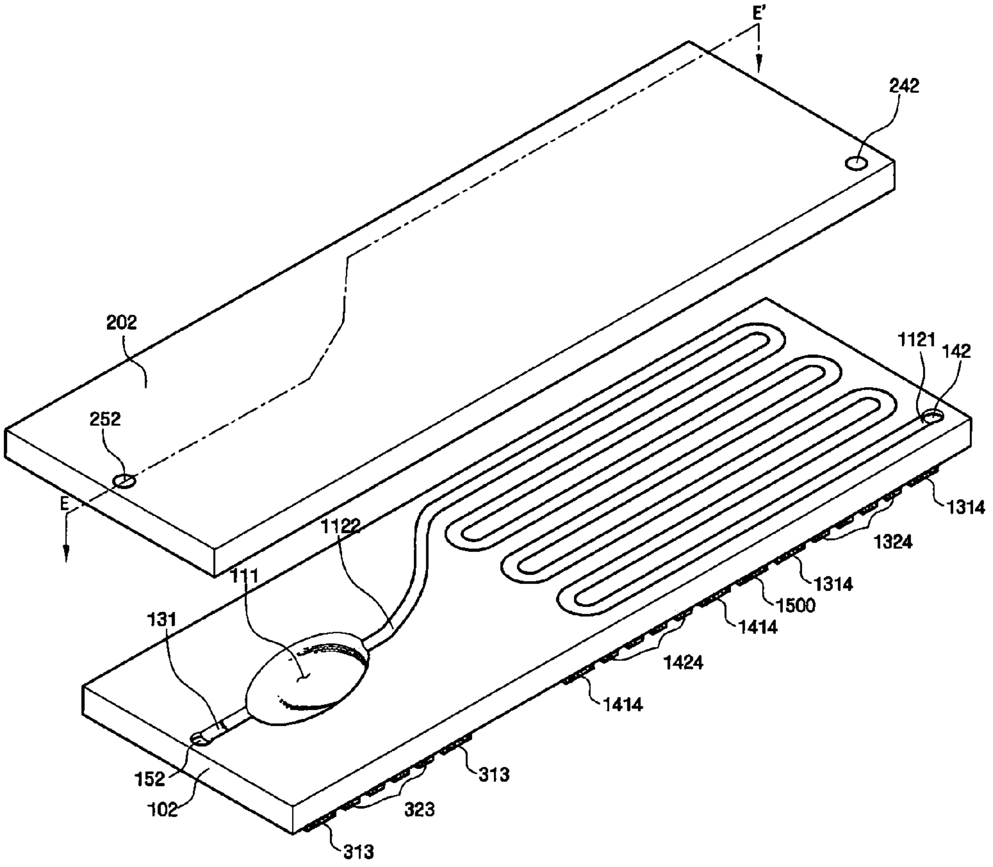
FIG. 16 is an exploded perspective view of a nucleic acid amplification apparatus according to a sixth embodiment.
Figure 17:
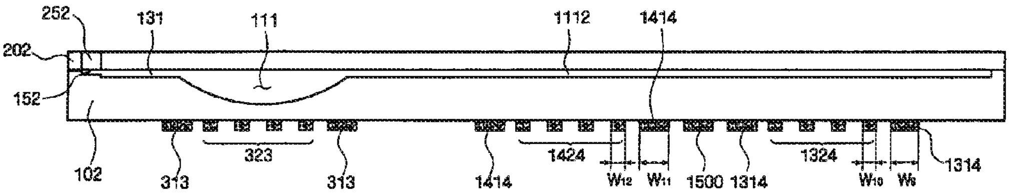
FIG. 17 is a cross-sectional view taken along line E-E' of FIG. 16.

Hereinafter, a nucleic acid amplification apparatus according to a sixth embodiment will be described in detail with reference to FIGS. 16 and 17. FIG. 16 is an exploded perspective view of a nucleic acid amplification apparatus according to a sixth embodiment of the present invention, and FIG. 17 is a cross-sectional view taken along line E-E' of FIG. 16.

The current embodiment is substantially the same as the fifth embodiment in that a cell lysis space 1112 further includes preliminary cooling units 1414 and 1424 and a heat insulation unit 1500 and the cell lysis space 1112 has a shape different from that of the cell lysis space 1111 of the fifth embodiment.

The preliminary heating units 1314 and 1324 according to the current embodiment may have substantially the same shape and arrangement as those of the previous embodiments. For example, the preliminary heating units 1314 and 1324 may be disposed on a bottom surface of a substrate 102 or on a bottom surface of a cover unit 202.

The preliminary cooling units 1414 and 1424 according to the current embodiment are disposed below or above the cell lysis space 1112 and eliminate heat from the cell lysis space 1112. Specifically, the preliminary cooling units 1414 and 1424 may be disposed on the bottom surface of the substrate 102 so as to be spaced apart from the preliminary heating units 1314 and 1324. Alternatively, the preliminary heating units 1314 and 1324 may be disposed on the bottom surface of the substrate 102 while the preliminary cooling units 1414 and 1424 may be disposed on the bottom surface of the cover unit 202. The preliminary cooling units 1414 and 1424 may include a plurality of first preliminary cooling units 1414 and a plurality of second preliminary cooling units 1424, which are arranged substantially in parallel with each other. Like the preliminary heating units 1314 and 1324, heat absorption quantities of the first preliminary cooling units 1414 disposed at the outermost portions of the cell lysis space 1112 may be larger than heat absorption quantities of the second preliminary cooling units 1424 disposed at a central portion of the cell lysis space 1112. In more detail, an area of each of the first preliminary cooling units 1414 may be greater than an area of each of the second preliminary cooling units 1424. In addition, a width $w_{11}$ of each of the first preliminary cooling units 1414 is greater than a width $w_{12}$ of each of the second preliminary cooling units 1424. Accordingly, the temperature distribution of the cell lysis space 1112 can be made to be uniform during a cooling process.

The cell lysis space 1112 of the current embodiment may be channel-shaped. The cell lysis space 1112 is formed such that a cell sample is allowed to alternately flow above and below a region where the preliminary heating units 1314 and 1324 are arranged and a region where the preliminary cooling units 1414 and 1424 are arranged. In more detail, the cell lysis space 1112 includes a first direction channel through which the sample flowing from the preliminary heating units 1314 and 1324 to the preliminary cooling units 1414 and 1424 and a second direction channel through which the sample flowing from the preliminary cooling units 1414 and 1424 to the preliminary heating units 1314 and 1324, and the first and second direction channels are alternately arranged to be connected to each other. That is to say, the cell lysis space 1112 may be formed in a serpentine shape such that the sample alternately flow through the preliminary heating units 1314 and 1324 and the preliminary cooling units 1414 and 1424. A difference between a temperature of the cell lysis space 1112 heated by the preliminary heating units 1314 and 1324 and a temperature of the cell lysis space 1112 cooled by the preliminary cooling units 1414 and 1424 may range from about 50 to about 200° C. For example, the heating temperature may range from about 90° C. to about 100° C., and the cooling temperature may range from about 30° C. to about −30° C.

The cell lysis space 1112 undergoes repeated cycles of rapid cooling and rapid heating while alternately passing through the preliminary heating units 1314 and 1324 and the preliminary cooling units 1414 and 1424, thereby facilitating cell lysis.

A heat insulation unit 1500 may further be provided between the region where the preliminary heating units 1314 and 1324 are arranged and the region where the preliminary cooling units 1414 and 1424 are arranged. For example, the heat insulation unit 1500 may be disposed between the preliminary heating units 1314 and the first preliminary cooling units 1414 and allows the cell lysis space 1112 to undergo a rapid temperature change, rather than a smooth, linear temperature change, thereby increasing the cell lysis effect.

While the fifth and sixth embodiments illustrate that cell lysis is performed using the preliminary heating units 1314 and 1324, methods of performing cell lysis are not limited to the illustrated examples, using a mechanical method, such as an ultrasonic method, a pressurizing method (using a French press, etc.), a depressurizing method, or a pulverization method, or non-mechanical method, such as a chemical method, a thermal method, or an enzymatic method.

For example, a cell solution or suspension is placed in a chamber positioned in an ultrasonic bath to perform ultrasonic treatment, thereby mechanically lysing cell. Alternatively, cell lysis may also be performed such that cells are allowed to colliding with projecting portions of an LOC. Further, cell lysis may be performed such that a lipid bilayer is destroyed using a detergent, such as an acid, a base, a cleanser, a solvent, or a chaotropic material, and intracellular structures are released. Another way of performing cell lysis is to lyse cells chemically by lysing membrane protein. An enzymatic method using an enzyme, such as lysozyme or protease, may also be employed in performing cell lysis.

The released nucleic acids resulting from cell lysis are introduced into the reaction space 111 maintained at a uniform temperature by heating units 313 and 323 and then amplified.

The nucleic acid amplification apparatus according to the current embodiment can operate in the following manner. A cell mixture introduced throughout an inlet port 242 of the cover unit 202 is transferred to the cell lysis space 1112 via an inlet well 142 and an inlet channel 1112. Cells transferred to the cell lysis space 1112 shaped of a channel are destructed while alternately passing through preliminary heating units 1314 and 1324 and preliminary cooling units 1414 and 1424, to then isolate, for example, DNAs. The isolated DNAs are introduced into the reaction space 111 through a connection channel 1122 together with other mixtures to then be amplified. Next, the amplified DNAs are subjected to reactions occurring in another space of an LOC, e.g., a space for a microfluidic electrophoresis, through an outlet channel 131, and then discharged through an outlet well 152 and an outlet port 252.

While the present invention has been particularly shown and described with reference to exemplary embodiments thereof, it will be understood by those of ordinary skill in the art that various changes in form and details may be made therein without departing from the spirit and scope of the present invention as defined by the following claims. It is therefore desired that the present embodiments be considered in all respects as illustrative and not restrictive, reference being made to the appended claims rather than the foregoing description to indicate the scope of the invention.

What is claimed is:

1. A nucleic acid amplification apparatus comprising:

a substrate providing a polymerase chain reaction space; and a plurality of heating units disposed adjacent the reaction space to transfer heat to the reaction space, wherein a width of the reaction space gradually increase from its outermost portion to its central portion, wherein the plurality of heating units arranged substantially in parallel with each other, and among the plurality of heating units, the heating units disposed adjacent outermost portions of the reaction space having the largest heat radiation quantity, wherein the heating units are conductive patterns and the conductive patterns having the largest area are disposed adjacent outermost portions of the reaction space and the conductive patterns having the smallest area are disposed adjacent the central portion of the reaction space.

2. The nucleic acid amplification apparatus of claim 1, wherein a width of each of the conductive patterns disposed adjacent the outermost portions of the reaction space is greater than innermost portions of the reaction space.

3. The nucleic acid amplification apparatus of claim 1, wherein the heating units are disposed on a bottom surface of the substrate and transfer heat to the reaction space.

4. The nucleic acid amplification apparatus of claim 3, further comprising:

a cover unit covering the reaction space and disposed above the substrate; and a plurality of cooling units disposed on a bottom surface of the cover unit to eliminate heat from the reaction space, wherein the plurality of cooling units are arranged substantially in parallel with each other, and the cooling units disposed adjacent outermost portions of the reaction space are capable of the largest amount of heat absorption.

5. The nucleic acid amplification apparatus of claim 4, wherein the cooling units are cooling coils, and the cooling coils disposed adjacent outermost portions of the reaction space are capable of the largest amount of heat absorption.

6. The nucleic acid amplification apparatus of claim 1, further comprising:

a cover unit covering the reaction space and disposed above the substrate, wherein the plurality of heating units are disposed on a bottom surface of the cover unit to transfer heat to the reaction space.

7. The nucleic acid amplification apparatus of claim 6, further comprising a plurality of cooling units disposed on a bottom surface of the substrate to eliminate heat from the reaction space, wherein the plurality of cooling units are arranged substantially parallel with each other, and the cooling units disposed adjacent outermost portions of the reaction space are capable of the largest amount of heat absorption.

8. The nucleic acid amplification apparatus of claim 1, further comprising:

a cell lysis space formed on the substrate connected to the reaction space; and a preliminary heating unit disposed adjacent the cell lysis space to transfer heat to the cell lysis space.

9. The nucleic acid amplification apparatus of claim 8, wherein the preliminary heating unit includes a plurality of preliminary heating units arranged substantially parallel with each other, the preliminary heating units disposed adjacent outermost portions of the reaction space have the largest area.

10. The nucleic acid amplification apparatus of claim 1, further comprising:

a cell lysis space formed on the substrate connected to the reaction space;

a preliminary heating unit disposed adjacent to the cell lysis space to transfer heat to the cell lysis space; and a preliminary cooling unit disposed adjacent to the cell lysis space so as to be spaced apart from the preliminary heating unit to eliminate heat from the cell lysis space, wherein the cell lysis space passes through regions where the preliminary heating unit and the preliminary cooling unit are provided.

11. The nucleic acid amplification apparatus of claim 10, wherein the preliminary heating unit includes a plurality of preliminary heating units arranged substantially in parallel with each other, outermost preliminary heating units having the largest area, and the preliminary cooling unit including a plurality of preliminary cooling units arranged substantially in parallel with each other, outermost preliminary cooling units having the largest area.

12. The nucleic acid amplification apparatus of claim 10, further comprising a heat insulation unit provided between a region where the preliminary heating unit is disposed and a region where the preliminary cooling unit is disposed.

13. The nucleic acid amplification apparatus of claim 10, wherein the cell lysis space includes a first channel through which the sample flows from the preliminary heating unit to the preliminary cooling unit and a second channel through which the sample flows from the preliminary cooling unit to the preliminary heating unit, and the first and second channels are connected to each other.

14. The nucleic acid amplification apparatus of claim 1, wherein the reaction space has an outlet side, and inlet channel and a central portion, the reaction space having a width gradually increasing from sides of the inlet channel, and from the outlet side to the central portion.

15. A nucleic acid amplification apparatus comprising:

a first substrate;

a polymerase chain reaction space recessed within one surface of the substrate;

an inlet channel formed on one surface of the substrate and connected to one end of the reaction space;

an outlet channel formed on one surface of the substrate and connected to the other end of the reaction space;

a conductive pattern disposed adjacent to the reaction space to transfer heat to the reaction space; and a second substrate disposed to cover the one surface of the substrate, wherein a width of the reaction space gradually increase from its outermost portion to its central portion, wherein the conductive pattern includes a plurality of patterns arranged substantially in parallel with each other on the other surface of the first substrate, the conductive patterns being disposed at a connected portion of the reaction space, and the inlet channel and a connected portion of the reaction space and the outlet channel having the largest width, and the conductive patterns having the smallest width are disposed adjacent the central portion of the reaction space.

16. The nucleic acid amplification apparatus of claim 15, further comprising:

a cooling coil formed on the other surface of the second substrate for eliminating heat from the reaction space, wherein the cooling coil includes a plurality of coils disposed substantially in parallel with each other, the coils disposed above a connected portion of the reaction space, and the inlet channel and a connected portion of the reaction space and the outlet channel having the largest width.

17. The nucleic acid amplification apparatus of claim 15, further comprising:

a cell lysis space formed on one surface of the substrate between the reaction space and the inlet channel;

a preliminary conductive pattern disposed adjacent the cell lysis space; and a connection channel formed on one surface of the first substrate connecting the cell lysis space with the reaction space, wherein the preliminary conductive pattern includes a plurality of conductive patterns disposed substantially in parallel with each other, the conductive patterns disposed at a connected portion of the reaction space and the inlet channel, or a connected portion of the reaction space and the connection channel, having the largest area.

18. The nucleic acid amplification apparatus of claim 15, further comprising:

a cell lysis space formed on one surface of the substrate disposed between the reaction space and the inlet channel;

a plurality of preliminary conductive patterns arranged adjacent the cell lysis space substantially parallel with each other to transfer heat to the cell lysis space;

a plurality of preliminary cooling coils arranged adjacent the cell lysis space substantially parallel with each other so as to be spaced apart from the preliminary conductive patterns and disposed at the outermost portions to eliminate heat from the cell lysis space; and a connection channel connecting the cell lysis space with the reaction space, wherein the preliminary conductive pattern or the preliminary cooling coil disposed at a connected portion of the cell lysis space and the inlet channel or a connected portion of the cell lysis space and the connection channel having the largest area.

* * * * *